United States Patent
Denolly

(10) Patent No.: US 8,211,066 B2
(45) Date of Patent: Jul. 3, 2012

(54) DEVICE FOR SELECTIVE ACCESS CLOSURE INSIDE A CATHETER

(75) Inventor: Pascal Denolly, Jardin (FR)

(73) Assignee: SEDAT, Irigny (FR)

( * ) Notice: Subject to any disclaimer, the term of this patent is extended or adjusted under 35 U.S.C. 154(b) by 426 days.

(21) Appl. No.: 11/276,341

(22) Filed: Feb. 24, 2006

(65) Prior Publication Data

US 2006/0178636 A1 Aug. 10, 2006

Related U.S. Application Data

(63) Continuation of application No. 10/489,195, filed as application No. PCT/FR02/02692 on Jul. 26, 2002, now abandoned.

(30) Foreign Application Priority Data

Sep. 11, 2001 (FR) ..................................... 01 11750

(51) Int. Cl.
*A61M 5/00* (2006.01)
(52) U.S. Cl. ......................................... 604/245; 604/48
(58) Field of Classification Search .................... 604/19, 604/48, 93.01, 164.01, 164.07, 245, 246, 604/247, 167.03
See application file for complete search history.

(56) References Cited

U.S. PATENT DOCUMENTS

| 4,943,280 | A | * | 7/1990 | Lander | 604/256 |
| 4,988,339 | A | * | 1/1991 | Vadher | 604/197 |
| 5,195,980 | A | | 3/1993 | Catlin | |
| 5,325,868 | A | | 7/1994 | Kimmelstiel | |
| 5,423,331 | A | | 6/1995 | Wysham | |
| 5,685,854 | A | | 11/1997 | Green et al. | |
| 5,827,202 | A | | 10/1998 | Miraki et al. | |
| 6,217,558 | B1 | | 4/2001 | Zadini et al. | |
| 6,235,000 | B1 | | 5/2001 | Milo et al. | |
| 6,458,103 | B1 | * | 10/2002 | Albert et al. | 604/167.03 |

FOREIGN PATENT DOCUMENTS

DE 42 13 691 A1 11/1993

* cited by examiner

*Primary Examiner* — Kevin C Sirmons
*Assistant Examiner* — Deanna K Hall
(74) *Attorney, Agent, or Firm* — Sughrue Mion, PLLC

(57) ABSTRACT

The device (10) for selective access closure inside a catheter comprises a conduit (14) having a rear extremity (16) for the insertion of a medical instrument and a mechanism (27) for adjusting the cross-section provided within the conduit (14). The mechanism (27) comprises a member (32) for repositioning the device between an opening movement and a closing movement. The direction of movement of the repositioning member (32) along both the closing path and the opening path are identical.

9 Claims, 12 Drawing Sheets

DEVICE FOR SELECTIVE ACCESS CLOSURE INSIDE A CATHETER

This is a continuation of application Ser. No. 10/489,195, filed Mar. 10, 2004, now abandoned (formalities completion date of Aug. 6, 2004) which was a National Stage Entry under 35 U.S.C. §371 of PCT/FR02/02692, filed Jul. 26, 2002. The entire disclosure of prior application Ser. No. 10/489,195, claiming the benefit of French Application No. 0111750, filed Sep. 11, 2001, is hereby incorporated by reference.

BACKGROUND OF THE INVENTION

This invention relates to a selective access closure device inside a catheter of the type comprising a body bounding a conduit having a rear extremity into which a medical instrument is inserted and a front extremity provided with means for connection to the catheter and also a mechanism for adjusting the passage cross-section within the conduit, this adjustment mechanism comprising a device to reposition means which can move with respect to the body along an opening path to bring about a change to an open condition in which a nominal passage cross-section is provided within the conduit and a closing path to bring about a change to a closed condition in which passage through the conduit is at least partly obstructed.

Such a device is in particular used in angioplasty procedures performed in cardiology. These procedures comprise shaping a blood vessel (vein or artery) which has become constricted, causing a reduction in blood flow. This shaping of the vessel is effected either through mere dilation of the vessel using an inflatable balloon or the fitting of a self-expanding tubular endoprosthesis currently known as a "stent".

Whatever the nature of the procedure, it is advantageous to act within the patient's circulatory system. For this purpose an incision is made in an artery, generally the femoral artery, and a catheter is inserted into it. The various instruments required for treating the vessel are delivered to the location for the procedure through travel within the circulatory system after having been inserted via the indwelling catheter in the femoral artery. More specifically a surgical guide comprising a long flexible metal wire, a balloon, a stent or another catheter may be inserted into the circulatory system through the prefitted catheter. In order to avoid excessive bleeding from the patient the catheter inserted in the femoral artery is provided at its free end with a selective closure device which will prevent the outflow of blood while making it possible for the various instruments necessary for the procedure to be inserted in the catheter.

Selective closure devices are already known. They generally comprise a diaphragm obstructing the passage provided within the body of the device. This diaphragm comprises for example an elastic seal. The device comprises an appropriate mechanism to cause deliberate opening of the seal in order to allow the instruments necessary for the procedure to be inserted. This mechanism generally comprises a sliding tubular member which can be moved between a position away from the seal and a position engaging the inner part of the seal, thus increasing its inner cross-section. The tubular member can for example be moved in lateral movement under the control of a rotating ring or a sliding cursor. The ring or cursor can be moved in one direction to bring about opening of the device and in the other direction to cause its closure.

Such a device is inconvenient to operate because the surgeon must use both hands, one to hold the body of the device and the other to move the ring or cursor.

SUMMARY OF THE INVENTION

The object of the invention is to provide a selective closure device which is easy to operate.

For this purpose the invention relates to a selective closure device of the aforesaid type characterised in that the directions of movement of the repositioning member along the said closing path on the one hand and the directions of movement of the repositioning member along the said opening path on the other hand are identical.

In accordance with particular embodiments the device comprises one or more of the following features:

- the direction of movement of the repositioning member along the said opening and closing paths is angularly offset in relation to the axis of the conduit,
- the said mechanism for adjusting the cross-section of the passage provided within the conduit comprises a diaphragm and a cannula fitted so as to move within the conduit between a position away from the diaphragm, corresponding to the closed condition of the device, and an engaged position through the diaphragm, corresponding to the open condition of the device, and the mechanism comprises means for moving the cannula alternately in one direction and the other between its two positions under the control of the repositioning member only when the repositioning member is moved, following the said opening and closing paths, in a control direction which is identical for the two directions of movement of the cannula,
- the conduit is straight, and the said repositioning member can be moved laterally between the said opening and closing directions of travel parallel to the axis of the said conduit,
- the mechanism for adjusting the cross-section of the passage provided within the conduit comprises both a slide with which the cannula forms an integral part, the said slide being capable of being caused to slide in relation to the body under the control of the said repositioning member and a ratchet wheel rotatably mounted with respect to the slide and fixed axially with respect to the latter, the body comprising shaped sections engaging the ratchet wheel to move it angularly as the slide is caused to slide, and guide sections for the ratchet wheel to guide it when the said repositioning member is released towards at least two different axial positions corresponding to the open and closed conditions of the device,
- the said repositioning mechanism comprises a resilient member to return the repositioning member along the said opening and closing paths in the direction opposite to that causing switching of the device,
- the body has a generally flattened oval shape with two opposing main surfaces and a peripheral lateral surface joining the said opposing main surfaces,
- on its peripheral lateral surface the body has at least two adjacent hollows forming supporting surfaces for the fingers of the hand,
- two hollows forming supporting surfaces for the fingers of the hand are located in succession in a direction substantially parallel to the axis of the conduit,
- the said control member projects outside the casing between two hollows forming the supporting surfaces for the fingers of the hand and the rear extremity of the conduit, and
- it comprises means for holding the device in its open condition and its closed condition.

BRIEF DESCRIPTION OF THE DRAWINGS

The invention will be more particularly understood from a reading of the following description provided purely by way of example and making reference to the following drawings, in which.

DETAILED DESCRIPTION OF THE INVENTION

Figure 1:
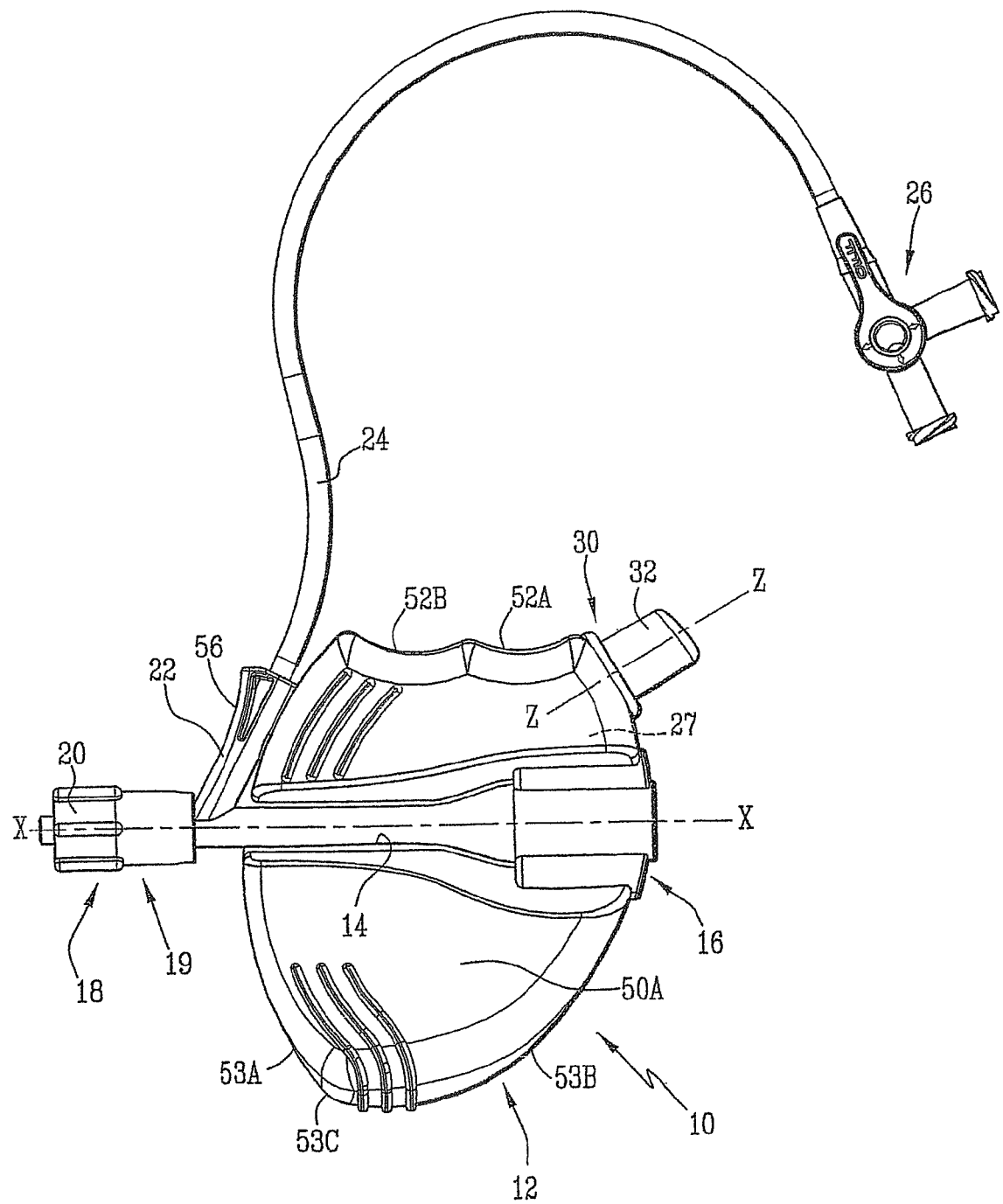
FIG. 1 is a view in elevation of the selective closure device according to the invention.

Selective closure device 10 is shown laid flat on a surface in FIG. 1. This device comprises a body 12 bounding a transverse conduit 14 for the passage of a filiform instrument intended to be inserted into the human body. Body 12 has the general shape of a flattened oval so that it can be held in the hand.

Conduit 14 is straight having an axis X-X. It passes through body 12 from one side to the other and opens at its two extremities. Conduit 14 has a rear extremity 16 for the insertion of filiform treatment instruments. At its front extremity, identified as 18, conduit 14 comprises means 19 for connection to a catheter extending the conduit. This connection means comprises for example a rotating ring 20 which can act together with a matching end-piece provided in the end of the catheter.

In the embodiment illustrated a branch 22 opens into conduit 14 in the vicinity of extremity 18 of the catheter connection. This branch 22 is extended by an auxiliary catheter 24, the free end of which is fitted with a three-way tap 26 through which fluid can be inserted into or drawn from the catheter regardless of the closure condition of the device.

Device 10 comprises a mechanism 27 for adjusting the passage cross-section provided through conduit 14. Within conduit 14 this mechanism comprises means 28 for selective closure of the conduit. These may be seen in FIG. 2. Also adjustment mechanism 27 comprises a repositioning mechanism 30 designed to control closure means 28 so as to reposition them between an open condition in which a nominal passage cross-section is provided through conduit 14 and a closed condition in which the passage through conduit 14 is at least partly obstructed.

This repositioning mechanism 30 comprises a repositioning member 32 comprising for example a push-button which can be moved along an opening path to effect a change to the open condition and a closing path to effect a change to the closed condition.

According to the invention the directions of movement of the repositioning member along both the closing path and the directions of movement of the repositioning member along the opening path are identical. In particular, in order to bring about opening or closure of the device repositioning member 32 is inserted into body 12 of the device in each case.

The device, and in particular its constituent components will now be described in greater detail with reference to FIG. 2 and the subsequent figures.

Figure 3A:
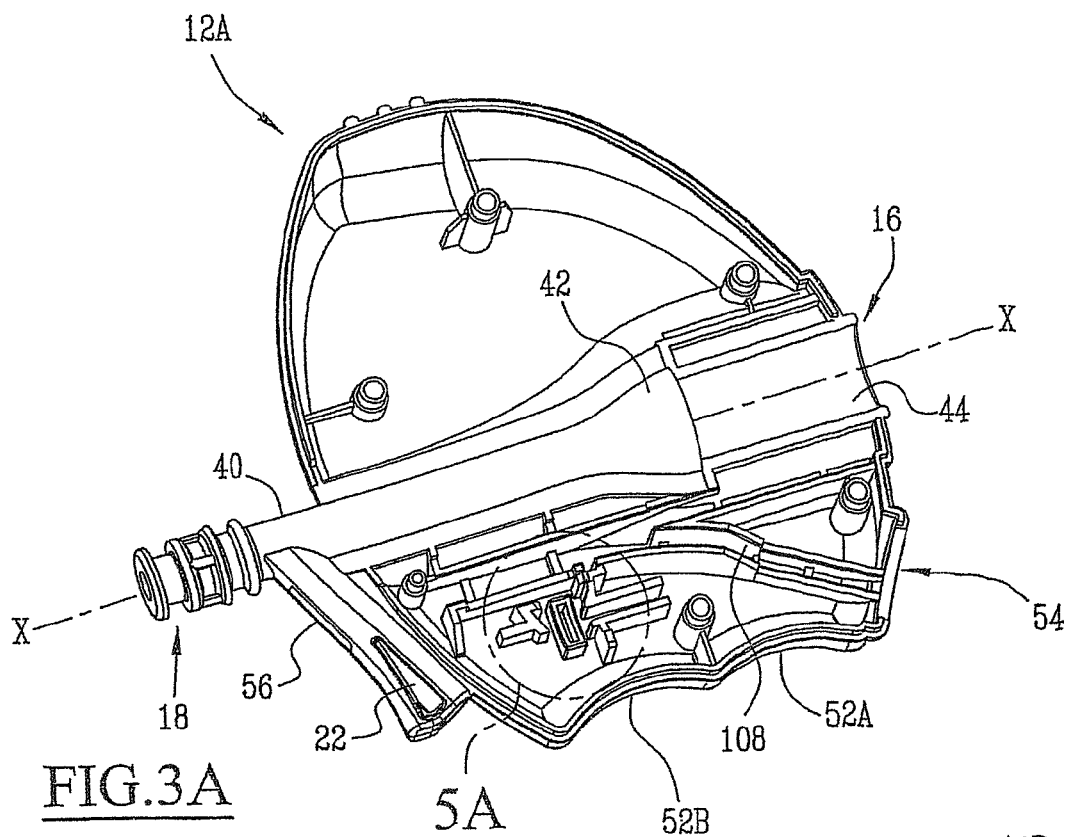

Body 12 comprises two half-shells 12A, 12B connected together along a median longitudinal plane. First half shell 12A, comprising a principal half-shell, is illustrated alone in FIG. 3. This half-shell is formed of a single piece of plastics material. In its median part it has a tubular section 40 having an axis X-X bounding conduit 14 over part of its length, and in particular the part thereof located on the side of front extremity 18. This tubular section 40 has in the median part of the half-shell a diverging section 42 of cross-section progressively increasing in the direction of rear extremity 16 of the conduit. This divergent section 32 is extended axially by a hemicylindrical section 42 to delimit half the extension of conduit 14.

Figure 3B:
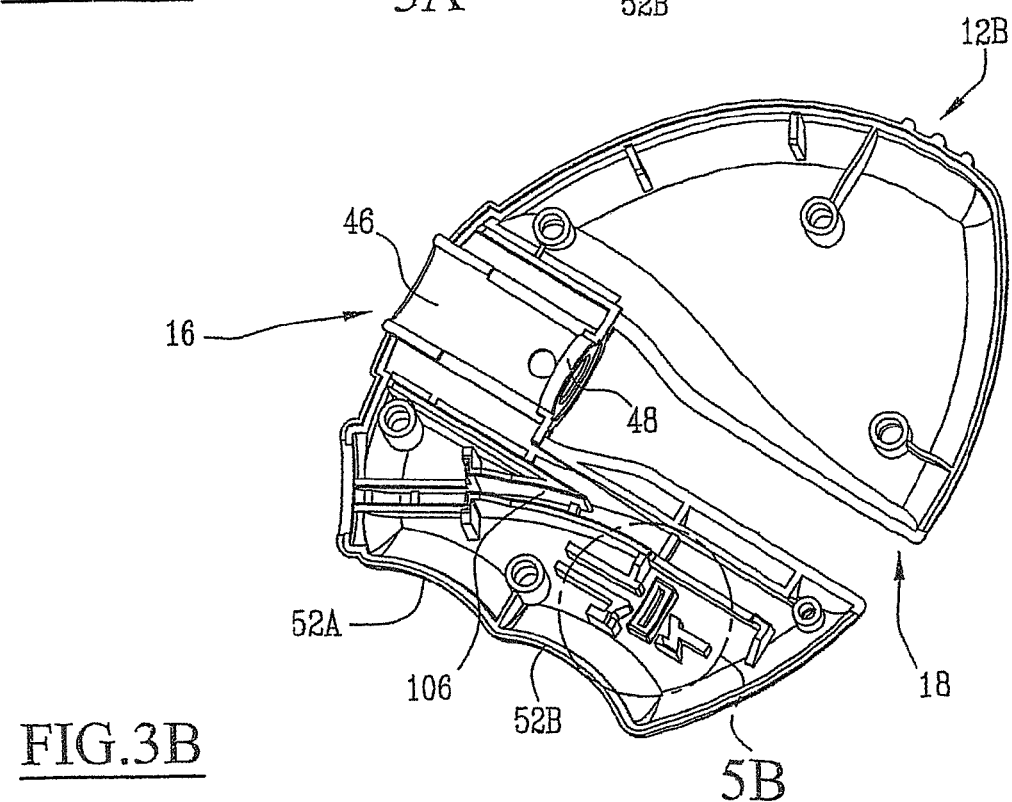

Complementary half-shell 12B, which is shown alone in FIG. 3B, has a hemicylindrical section 46 complementing hemicylindrical section 44 designed to delimit conduit 14 in the region of rear extremity 16. In the median part conduit 14 has a seat 48 for holding obstruction means 28. This seat is of one piece with complementary half-shell 12B at the end of hemicylindrical section 46.

Body 12 has a generally flattened oval shape. It has two main opposite surfaces 50A, 50B which generally extend parallel to each other and are defined by the two half shells 12A, 12B respectively.

Surface 50B defined by half shell 12B is generally flat. Surface 50A defined by principal half-shell 12A is generally curved outwards so that body 12 can be grasped with it resting in the hollow of the hand.

On the same side of conduit 14, and along a plane generally extending parallel to the X-X axis of the conduit, body 12 has two successive hollows 52A, 52B in its peripheral lateral surface intended to form supports for two consecutive fingers of one hand. On the side opposite finger supports 52A, 52B with reference to conduit 14, body 12 has a first and second convex surfaces 53A, 53B along its lateral surface, each designed to provide support for the palm of the hand. These two surfaces join at a point of inflection 53C formed by the apex of the casing furthest away from conduit 14.

Between rear extremity 16 of the conduit and the two finger supports 52A, 52B an orifice 54 is provided in casing 12 for the passage of push-button 32. Orifice 54 thus opens towards the exterior on the side of rear extremity 16.

Furthermore, in the vicinity of front extremity 18 of the conduit which is designed for connection to the catheter, body 12 has a third surface 56 providing finger supports. In the embodiment illustrated this surface 56 is provided on the lateral surface of branch 22 and is on the same side of conduit 14 as hollows 52A and 52B.

Figure 2:
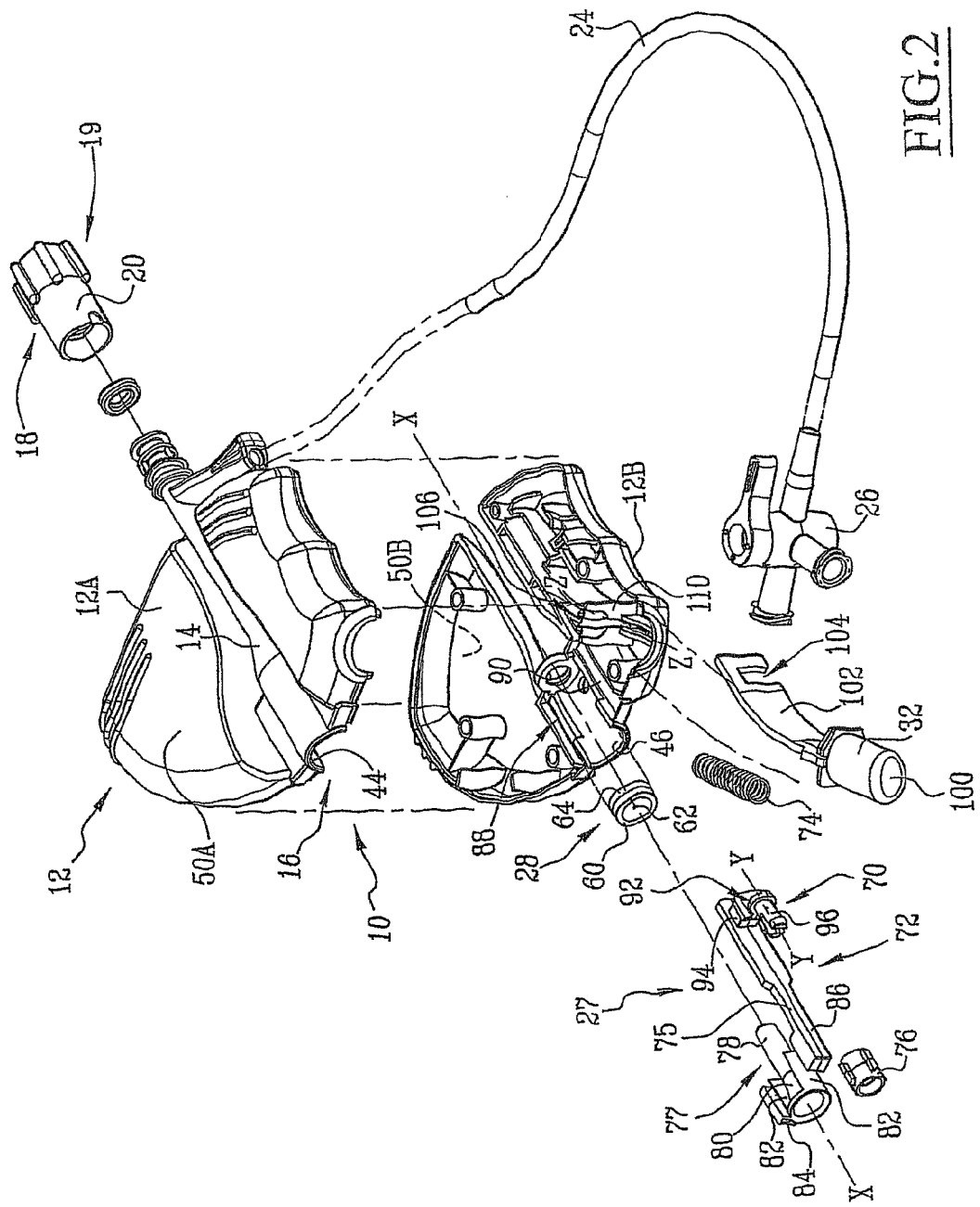
FIG. 2 is an exploded perspective view of the device in FIG. 1, FIGS. 3A and 3B are perspective views of the principal half-shell and the complementary half-shell of the casing of the device in FIGS. 1 and 2 respectively, these shells being shown with their inner surfaces visible.

As illustrated in FIG. 2, obstructing means 28 comprise a diaphragm comprising two seals joined side by side. A first seal 60 has a concave surface facing the rear extremity 16 of the conduit. This seal 16 is pierced axially by a hole 62 which is normally closed when the seal is at rest. Second seal 64 has three straight notches extending radially which join at the centre of the seal. These three notches are offset angularly by 120° C. and form a star.

Repositioning mechanism 30 for changing the condition of seals 60 and 64 comprises a movable assembly 72. This can move laterally parallel to the X-X axis of conduit 14. In addition to movable assembly 72 mechanism 30 comprises push-button 32 and a spring 74 which presses the push-button towards a resting position.

More specifically, movable assembly 72 comprises a slide 75 supporting a ratchet wheel 76 rotatably mounted about an axis Y-Y extending parallel to the X-X axis. This ratchet wheel is designed to act together with engaging sections provided in half-shells 12A and 12B. These sections will be described below in the description.

Slide 75 comprises, as may also be seen in FIGS. 6 to 9, a cannula 77 designed to engage axially within seals 60 and 64 so as to increase their inner passage cross-section. Opposite the seals it has a cylindrical sleeve 78 extended by a frustoconical section 80 which flares progressively away from sleeve 78. This frustoconical section 80 internally defines a guide surface which assists the insertion of operating instruments into the device.

Cannula 77 is bounded on either side by two curved plates 82 having generally cylindrical outer surfaces which are designed to ensure centering by acting together with the part of conduit 14 defined by hemicylindrical sections 44 and 46.

In addition to this, plates 82 are connected on either side to guide beams 84, 86 designed to engage in straight guide channels 88, 90 defined in the two half-shells 12A, 12B parallel to the X-X axis of conduit 14. These guide beams are designed to ensure sliding movement of movable assembly 72 with respect to body 12, and in particular with respect to conduit 14 in the direction of axis X-X.

Beam 86 extends beyond cannula 77 as far as a front extremity fitted with a bracket 92 designed to support ratchet wheel 76. This bracket has a base 94 supporting a pin 96 which extends along the Y-Y axis on which ratchet wheel 76 engages so as to be free to rotate. Pin 96 has a longitudinal slot and at its free end catches securing ratchet wheel 76 which elastically grips pin 96.

Push-button 32 has an operating head 100 of generally cylindrical shape designed to slide through orifice 54 and project outside the casing. This head 100 is extended by a generally curved elastic blade 102. At its free end blade 102 has a notch 104 in which the base 96 of the post engages to ensure that movable assembly 72 and push-button 32 are secured together.

Half-shells 12A and 12B each have a groove 106, 108 for guiding blade 102. These grooves are generally incurving in their median part in order to allow concomitant movements of both push-button 32 along an axis Z-Z angularly offset with respect to the X-X axis of conduit 14 and the free end of the blade connected to moving assembly 72 through notch 104 along the direction of the X-X axis.

The angle defined between the X-X and Z-Z axis lies between 20° and 60°, and is for example 30°.

Figure 6:
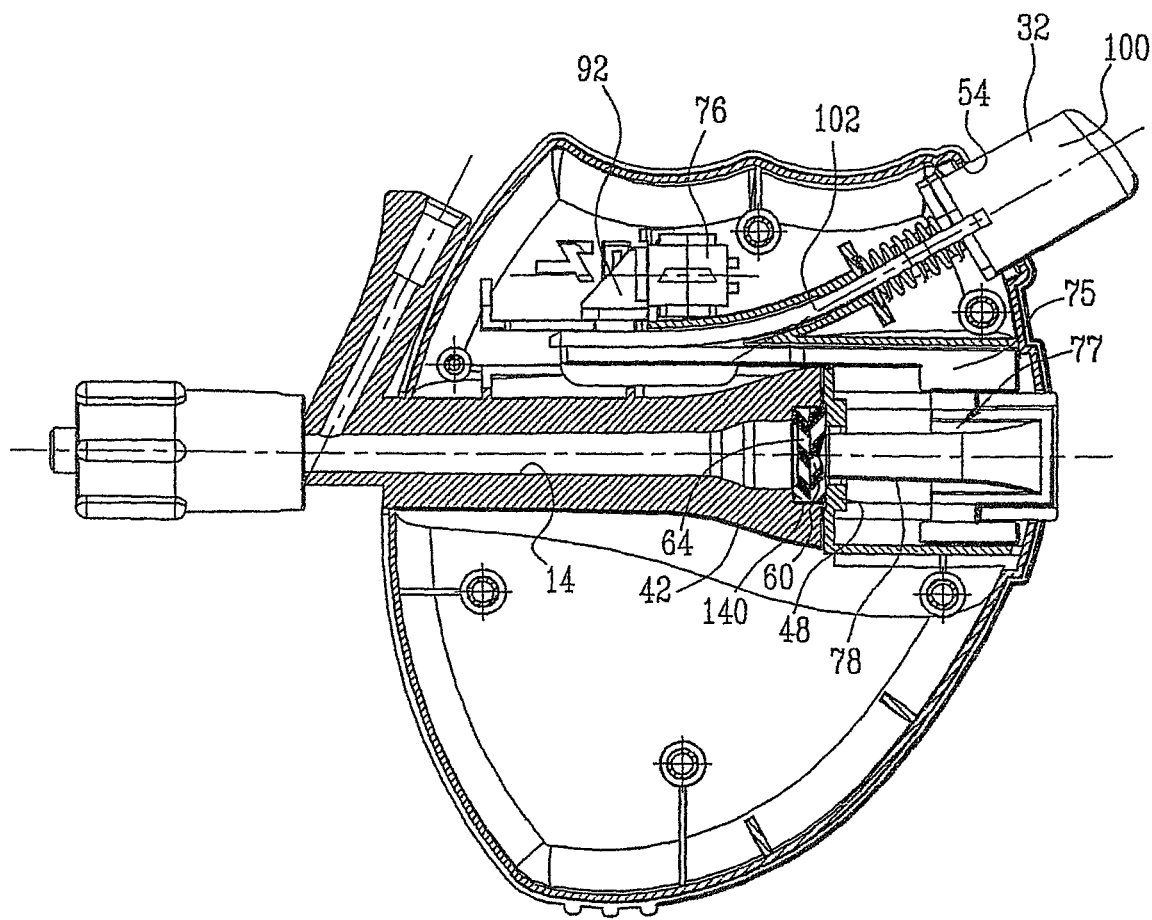
Figure 7:
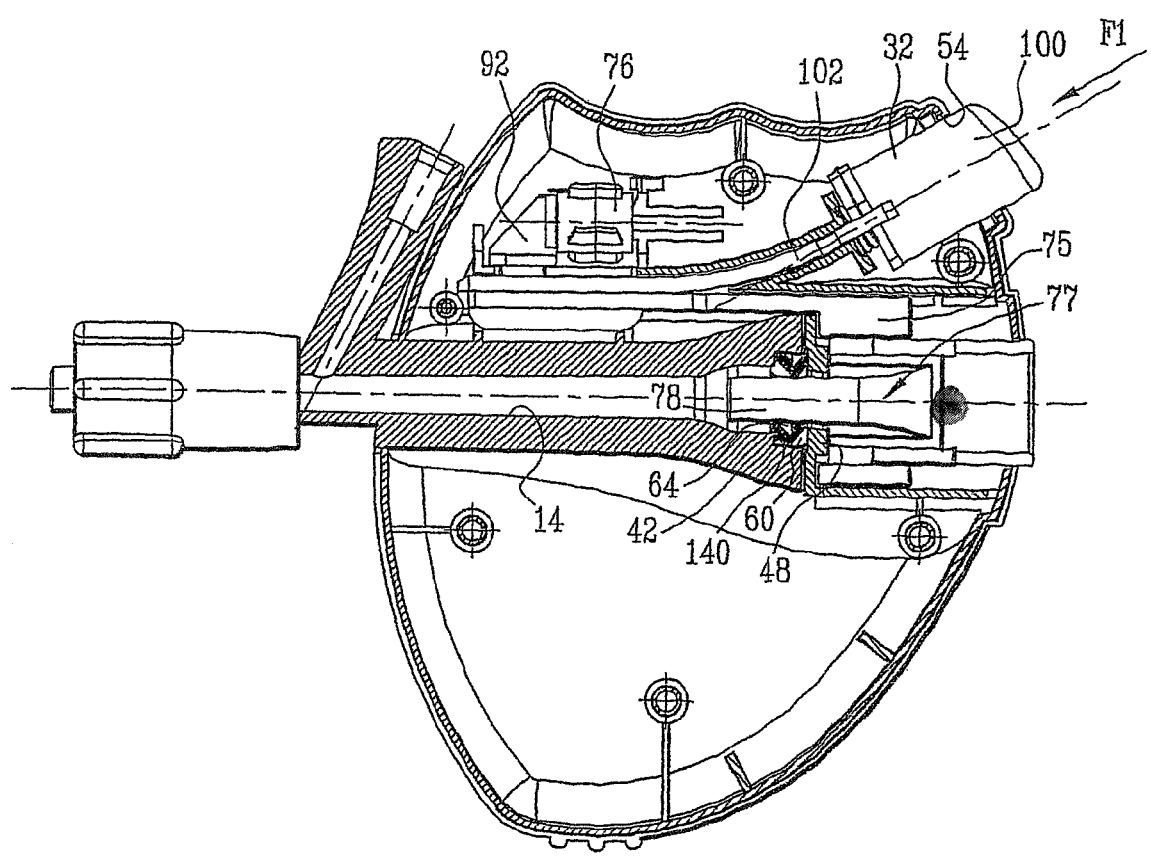
Figure 8:
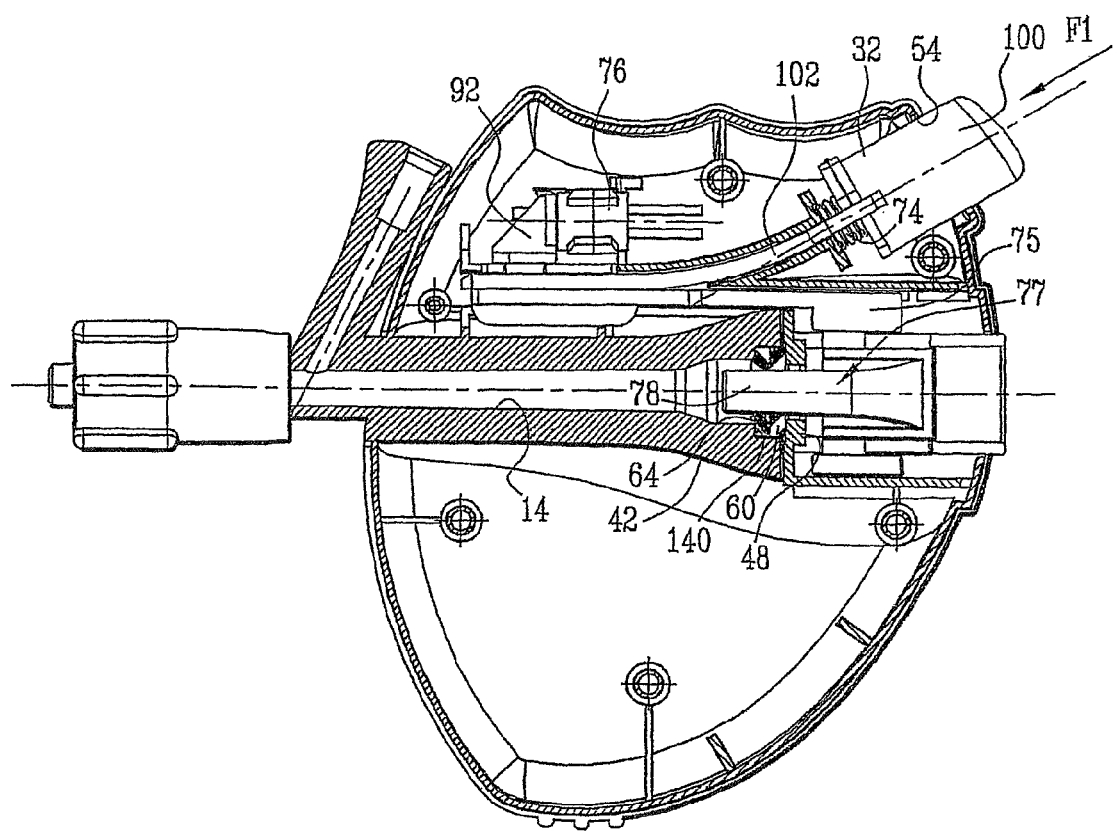
Figure 9:
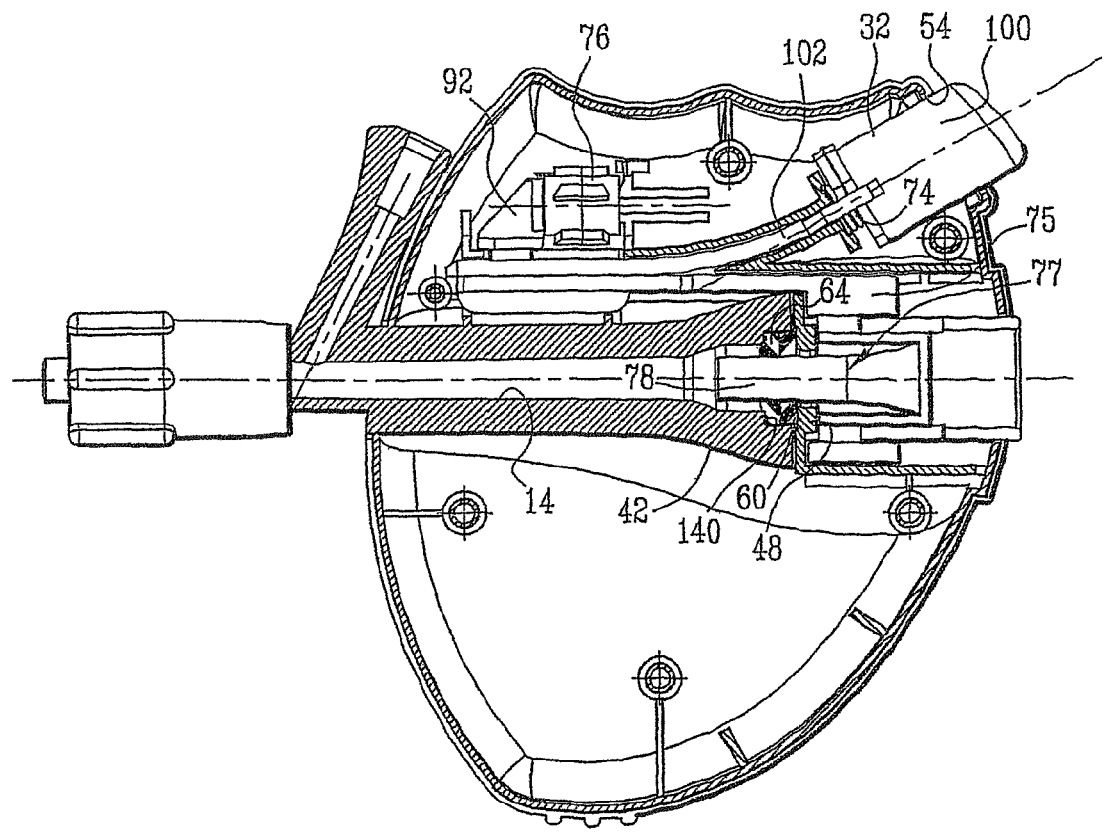

As illustrated in FIG. 6, spring 74 is a spiral compression spring engaged around elastic blade 102. One end of the spring bears against head 100 of the push-button and the other end bears against a wall 110 provided in complementary half-shell 12B opposite opening 54.

Ratchet wheel 76 is designed to act together with cam surfaces borne by the two half-shells 12A, 12B in order to constitute a back and forth control mechanism for movable assembly 72 brought about by a one-way movement of push-button 32.

Figure 4A:
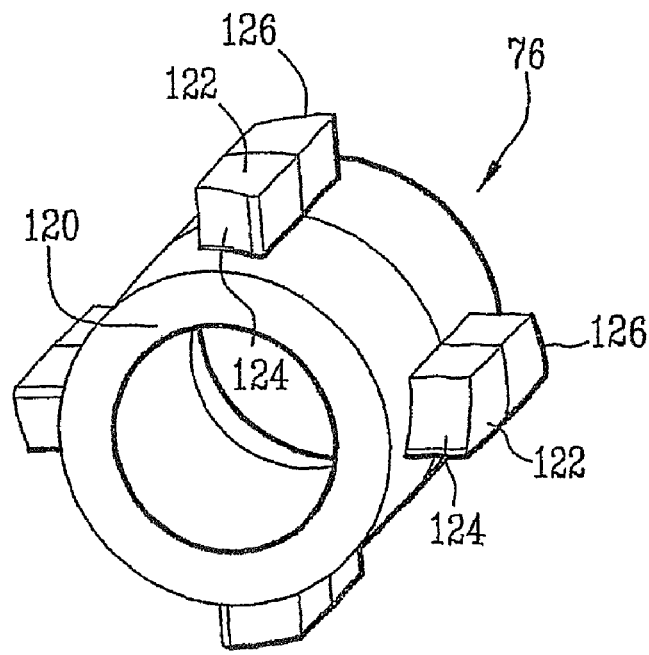
FIGS. 4A and 4B are perspective views of the same ratchet wheel seen from two opposite ends.
Figure 4B:
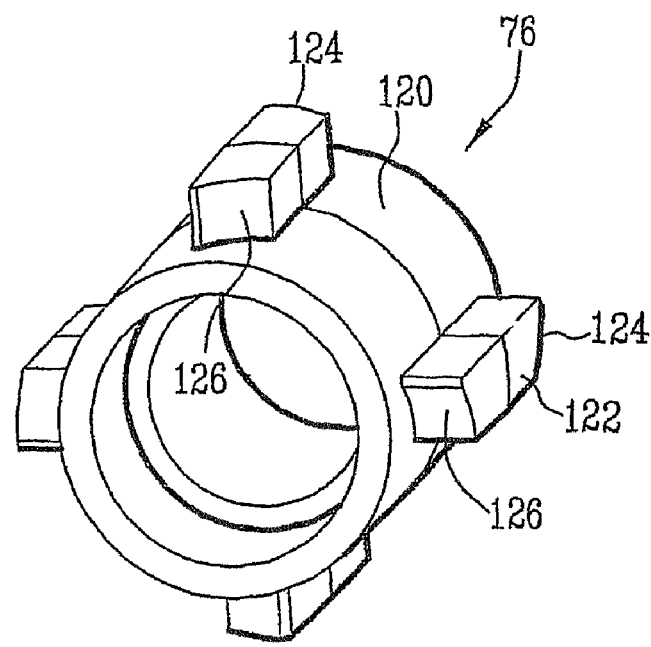

More specifically ratchet wheel 76, which is illustrated alone in FIGS. 4A and 4B, comprises a tubular sleeve 120 on the lateral surface of which there are four identical external ribs 122.

These ribs 122 extend along the generatrices of sleeve 120 and are angularly offset by 90°. The end surfaces of ribs 122 each have a ramp forming a cam surface.

The cam surfaces are generally inclined with respect to a plane extending perpendicularly to the axis of sleeve 120 and converge together in an anticlockwise direction when the front ends of the ribs identified as 124 face the observer as in FIG. 4A. The front ends of the ribs are those located opposite the base of pin 76 when ratchet wheel 76 is mounted on slide 74. The rear ends of ribs 120 are identified as 126. They may be seen in FIG. 4B.

Figure 5A:
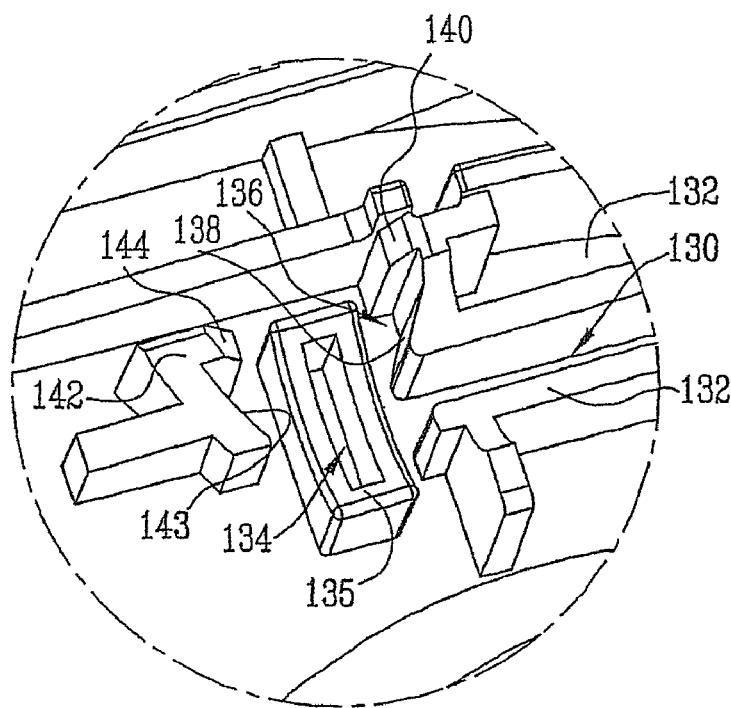
FIGS. 5A and 5B are views on a magnified scale of a detail of the principal and complementary half-shells respectively of the casing of the device in FIGS. 1 and 2, FIGS. 6, 7, 8 and 9 are views in longitudinal cross-section of the device according to the invention at different stages in operation.
Figure 5B:
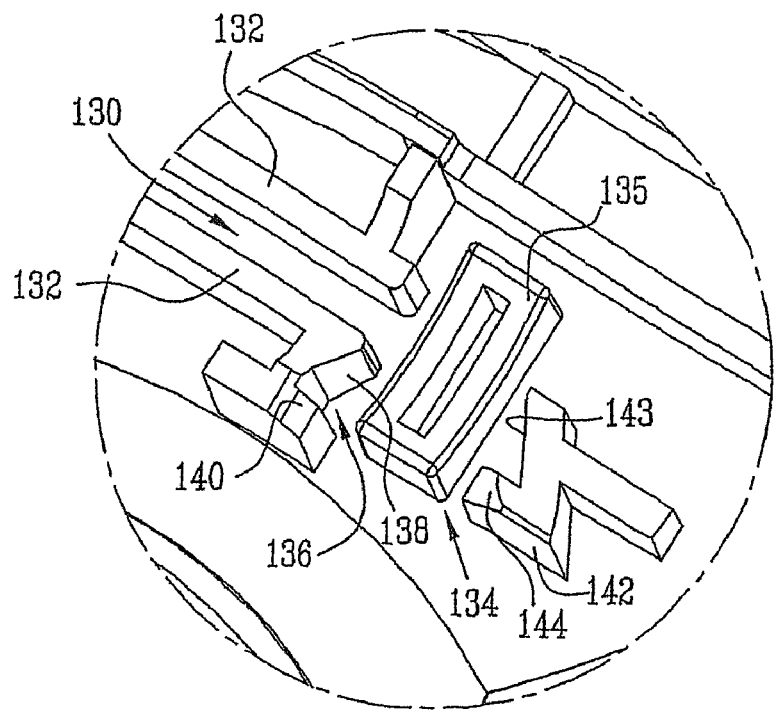

As illustrated in FIGS. 5A and 5B, the two half-shells 12A and 12B have projecting portions designed to act together with the cam surfaces specified at ends 124 and 126 of the ribs in order to cause ratchet wheel 76 to rotate when push-button 32 is pressed in, and projecting surfaces designed to ensure that the ratchet wheel is held in position when push-button 32 is released. The projections which ensure angular displacement of the ratchet wheel are designed to drive the latter always in the same direction.

The projecting portions of half-shells 12A and 12B are symmetrical with each other with respect to the Y-Y axis of rotation of ratchet wheel 76. These projections comprise a channel 130 on each half-shell 12A, 12B to receive ribs 122 of the ratchet wheel and thus ensure that rotation of the wheel is immobilised, two opposite ribs 122 being then held between the parallel sides identified as 132 bounding channels 130.

Each channel 130 is open at one end opening onto a surface 134 of rotational evolution of the ratchet wheel. This region 134 has a cradle 135 supporting (?) the ratchet wheel designed to guide the latter radially.

In the vicinity of the opening extremity of channel 130 a wall in each half-shell 12A, 12B has a cavity 136 to receive the rear end 126 of a rib to ensure axial and rotational immobilisation of ratchet wheel 76. This cavity 136 is bounded by a guide surface 138 connecting the end of one of the sides 132 to the base of cavity 136. This cavity 136 is designed to receive the rear end 126 of a rib and axially retain the ratchet wheel and moving assembly 172 in a position such that the device is open.

Cavity 136 is bounded on its wall opposite guide surface 138 by a pillar which has a cam surface 140 on its upper end which acts together with the cam surfaces of the rear ends 126 provided in the ribs of the ratchet wheel so as to cause the ratchet wheel to rotate through an angle of 22.5°.

Furthermore, on the other side of ratchet wheel evolution surface 134 and substantially opposite notch 136, a projection 142 in the half-shell has a first cam surface 143 which is substantially symmetrical with cam surface 138 and a second cam surface 144 which is substantially symmetrical with cam surface 140. These cam surfaces 143 and 144 are each designed to act together with a cam surface provided in the front end 124 of the ratchet wheel so as to cause the ratchet wheel to rotate through 22.5°.

When the device is assembled it is as illustrated in FIGS. 4 to 10. In particular seals 60 and 64 are confined within conduit 14, being received within a facing member 140 formed on the end of frustoconical section 42 obstructed by seat 48.

Cannula 77 extends along the axis of conduit 14 between its rear extremity 16 and seals 60 and 64. The head 100 of the push-button projects outside the body through opening 54, while blade 102 is engaged in the slide bounded by grooves 106 and 108. The end of blade 102 bearing notch 104 is engaged around base 94. Ratchet wheel 76 is borne by pin 96 along the Y-Y axis and extends opposite the guide projections provided in the two half-shells.

The device is in its closed position in FIG. 6. In this position head 100 of the push-button projects beyond body 12 to its full height and cannula 77 is located away from seals 60 and 64. As no stress is applied to the latter they completely obstruct conduit 14 if no medical instrument is inserted in conduit 14. If a medical instrument is inserted, seals 60 and 64 then fit precisely around the medical instrument passing through them, thus ensuring a seal which avoids the risk of any outflow of blood.

In this position of movable assembly 72 and push-button 32 ratchet wheel 76 is located between channels 130, two opposite ribs 122 being received in the channels. Wheel 76 is then rotationally immobilised.

For a medical instrument to be inserted in the catheter seals 60 and 64 have to be open. For this purpose push-button 32 is pressed in the direction of arrow F1.

When push-button 32 is pushed in, movable assembly 72 is then driven by blade 102 in the direction of the front extremity of conduit 14. In particular cannula 77 penetrates through seals 60 and 64, thus increasing the cross-section provided for passage within conduit 14.

Furthermore, when push-button 32 is pressed in, ratchet wheel 76 is moved laterally forward along the Y-Y axis so that the front ends 124 of the ribs which are not engaged in channels 130 come into contact with cam surfaces 144 provided in the front of ratchet wheel evolution region 135. Through a cam effect the ratchet wheel is caused to turn through 22.5° so that it is moved into the position in FIG. 7.

Push-button 32 is then released. Under the action of spring 74 movable assembly 72 is caused to move backwards. During this movement the rear ends of opposite ribs 122 act together with guide ramps 138 in order to bring about a 22.5° angular movement of ratchet wheel 76 and bring the rear ends 126 of the two opposite ribs into cavities 136. As ribs 122 bear against the base of cavities 136 which constitute stops, ratchet wheel 76 cannot move further laterally. Movable assembly 72 is then immobilised in the position shown in FIG. 8, despite the action of spring 74.

The device is then in a stable position and conduit 14 is held open making it possible for medical instruments to be inserted through conduit 14.

In order to bring about closure of the device push-button 32 is again pressed in in the same direction, that is in the same direction as arrow F1 as in opening. Movable assembly 72 is then moved towards the front of conduit 14 to the position illustrated in FIG. 9. As it moves forward ratchet wheel 76 comes into contact with cam surfaces 144 through the front ends 124 of the two opposite ribs 122. Through a cam effect the ratchet wheel is moved angularly through 22.5°.

When push-button 32 is released again, the rear ends 126 of ribs 122 borne on the ratchet wheel come into contact with cam surfaces 140, then bringing about additional rotation of the ring through an angle of 22.5° C., through the cam effect, so that ribs 122 are in line with channels 130. Under the effect of return spring 74 opposite ribs 122 move along the length of channels 130 thus allowing the movable assembly to return backwards to the position illustrated in FIG. 6. In this position cannula 77 is at a distance from seals 60 and 64, thus ensuring that conduit 14 is closed.

Figure 10:
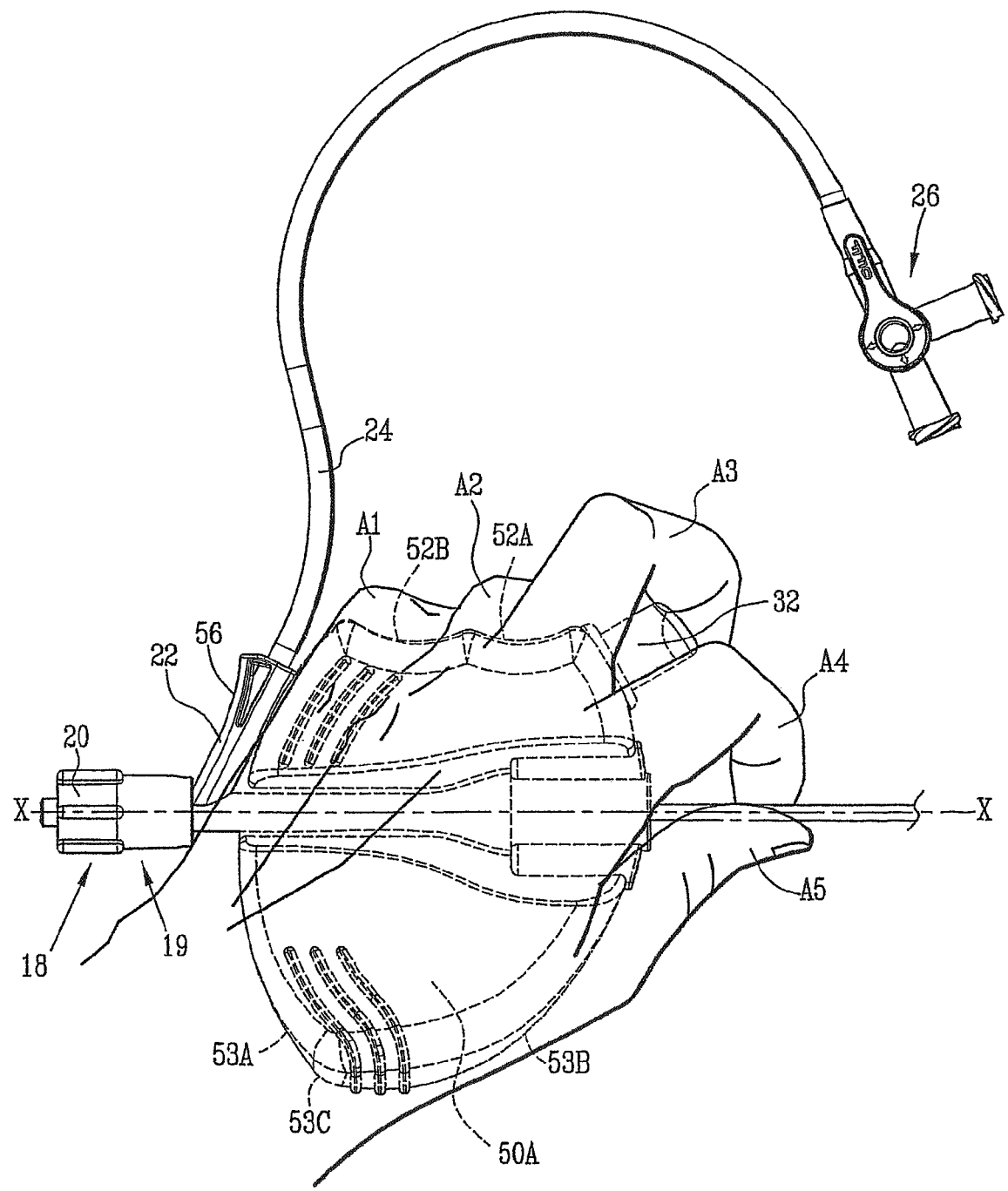
FIGS. 10, 11 and 12 are elevation views of the device held in the hand of a surgeon according to different ways of holding it.
Figure 11:
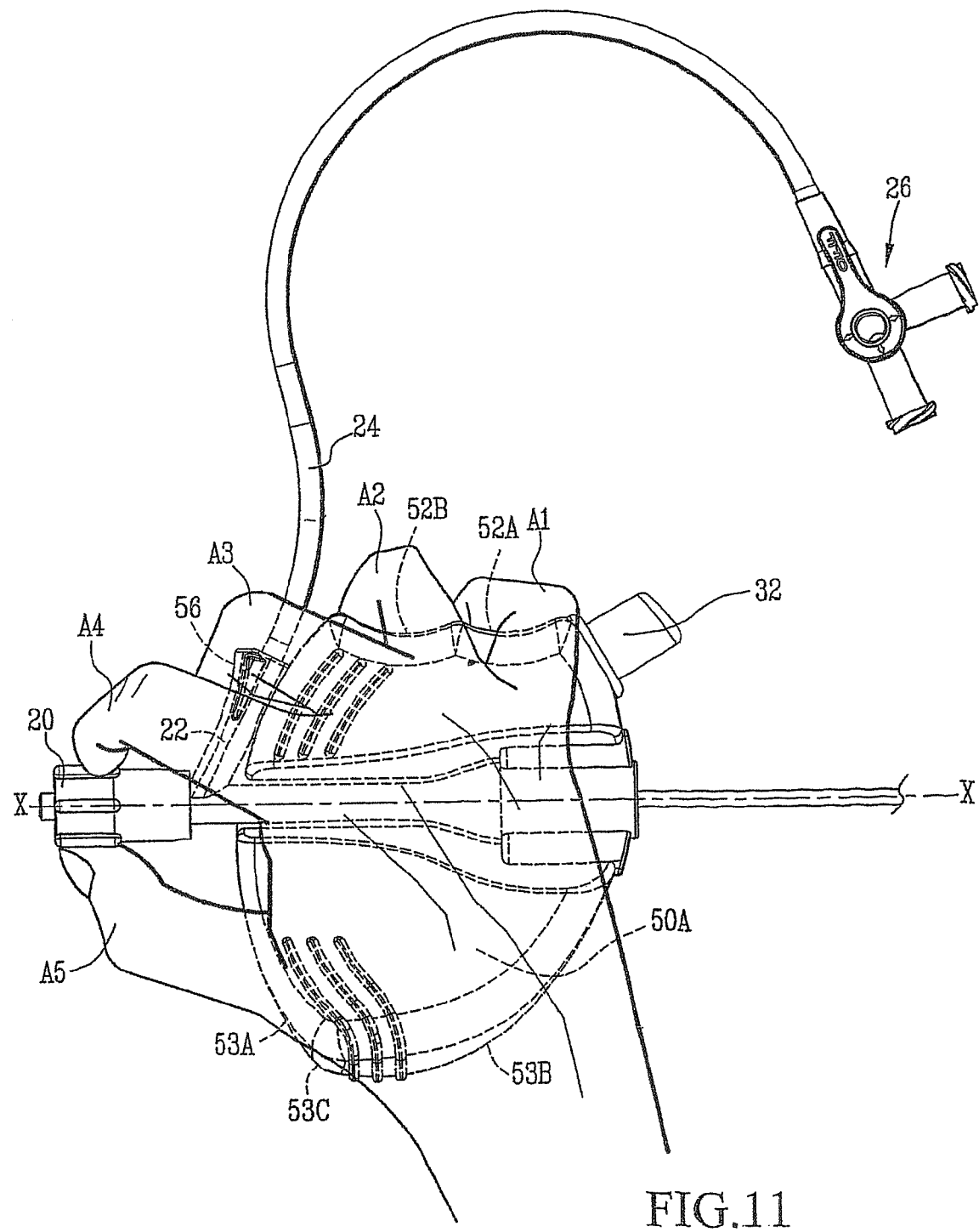
Figure 12:
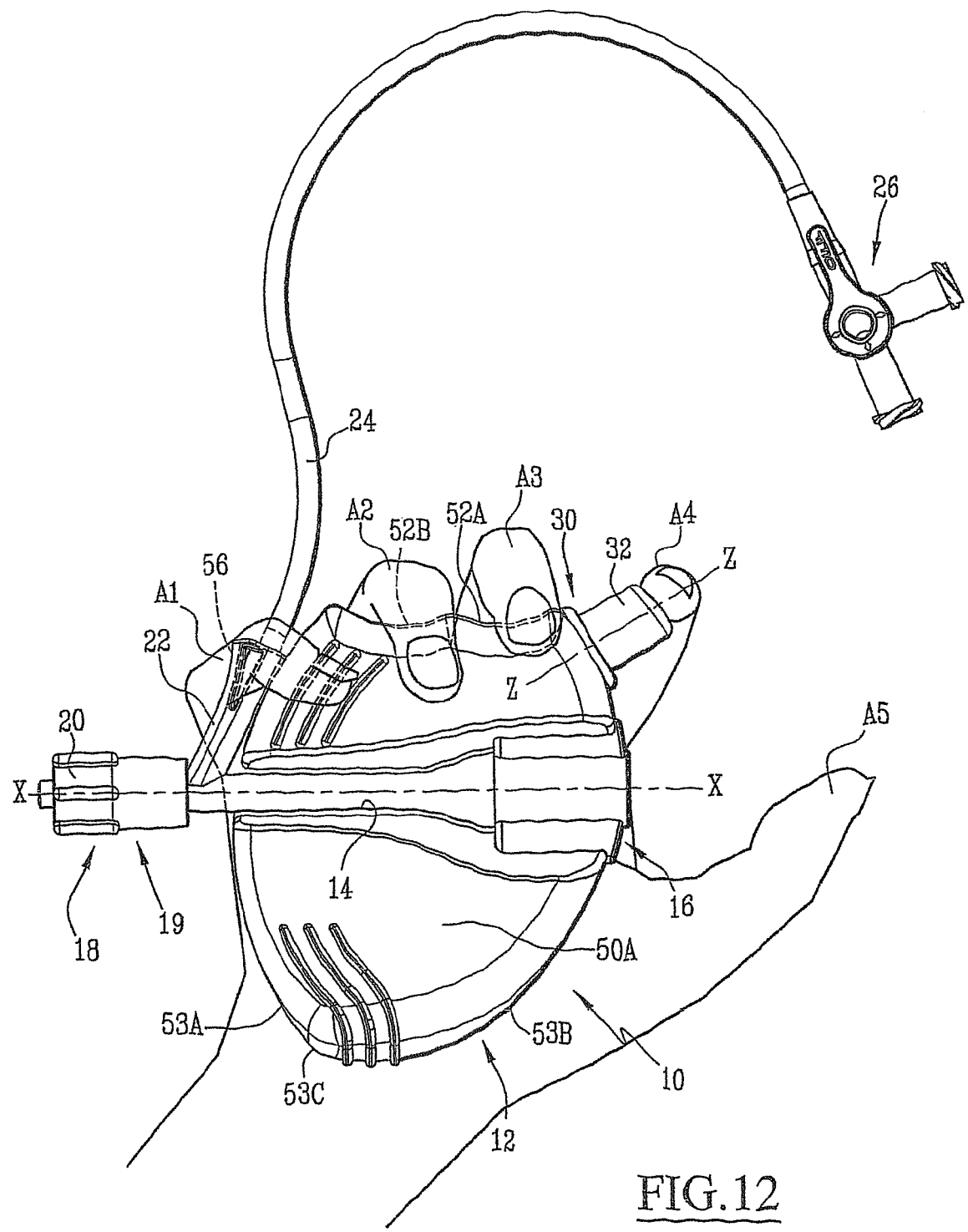

Ways of holding the device in the hand corresponding to different uses of the same are illustrated in FIGS. 10, 11 and 12.

More specifically, FIG. 10 illustrates how the device is held for the insertion of a filiform surgical instrument into the catheter and its use in an angioplasty procedure.

For this application the device is placed flat in the hollow of the hand with its flat surface 50A defined by half-shell 12A bearing against the inner surface of the left hand.

In order to ensure that it is stably held and push-button 32 and the surgical instruments inserted into the catheter can easily be controlled, little finger A1 is placed on finger support 52B and ring finger A2 is placed on finger support 52B so that middle finger A3 extends immediately over push-button 52 making it easy to press in and release the latter. The ends of the little finger and the ring finger are placed against the curved surface of the casing formed by complementary half-shell 12B. Index finger A4 and the thumb A5 extend substantially opposite the rear extremity 16 of conduit 14 and, as illustrated in FIG. 10, make it possible to hold a filiform instrument K which has been or is being inserted into the catheter between them. In this position supporting surface 53A bears against the palm of the hand so that casing 12 is gripped between little finger A1 and ring finger A2 on the one side and the palm of the hand on the other.

It will be understood that, as a result of the shape of the casing, and given the position of push-button 32, the device can be manipulated simply and conveniently using just one hand.

In particular, the device can easily be used by a single hand because button 32 is always operated in the same way in the same direction, whether for opening or closing the device.

FIG. 11 illustrates how the device is handled for coupling or uncoupling the catheter to or from front extremity 18 of the conduit. In order to do this body 12 of the device is held in the operator's right hand with its flat surface 50A defined by principal half-shell 12A supported in the hollow of the hand.

Little finger A1 is placed on finger support 52A, ring finger A2 is placed on finger support 52B and middle finger A3 is placed on finger support 56. Ring 20 then lies between index finger A4 and the thumb A5. The latter two fingers form a pincer which can cause ring 20 to rotate and thus connect or disconnect the catheter extending conduit 14. In this position the palm of the hand bears against supporting surface 53B so that body 12 is held between the three fingers A1, A2, A3 on the one side and the palm of the hand on the other.

FIG. 12 illustrates a final way of holding the device which can be used to clear bubbles from the catheter connected to the device. The operation of clearing bubbles consists of extracting any air bubbles which might be trapped in the catheter after it has been inserted. For this purpose conduit 14 must be opened momentarily without any filiform instrument being inserted through its rear extremity 16. In order to do this the device is held in the right hand with curved surface 50B defined by complementary half-shell 12B supported in the hollow of the hand.

Body 12 of the device is then held between little finger A1, ring finger A2 and middle finger A3 on the one side and the palm of the hand bearing against supporting surface 43B on the other side of conduit 14. More specifically, little finger A1 is placed on finger support 56, ring finger A2 is placed on finger support 52B and middle finger A3 is placed on finger support 52A. The ends of the three fingers A1, A2 and A3 are bent down onto the curved surface 50A of the body defined by principal half-shell 12A. Index finger A4 then extends immediately over push-button 32 allowing easy switching of the device between its open condition and its closed condition in order to clear bubbles from the catheter. When the device is handled in this way thumb A5 is not used and is held raised and then bent over onto the flat surface of principal half-shell 12A.

In these two latter modes of grasping the device it will also be understood that the controls which have to be manipulated, that is ring 20 or push-button 32, are immediately accessible to the finger or fingers, thus providing control, while the body of the device is firmly and reliably held in the surgeon's hand.

It will be noted that however the obstruction device is used it can be used by a single hand, thus leaving the surgeon's other hand free.

The invention claimed is:

1. Obstruction device for selective access closure inside a catheter comprising, on the one hand, a body bounding a conduit having a rear extremity for the insertion of a medical instrument and a front extremity provided with means for connection to the catheter and, on the other hand, a mechanism for adjusting the cross-section of the passage offered within the conduit, this adjustment mechanism comprising a member for repositioning the device which can move with respect to the body along an opening path to change to an open condition in which the nominal passage cross-section is provided within the conduit and along a closing path to change to a closed condition in which passage through the conduit is at least partly obstructed, wherein:

said mechanism for adjusting the passage cross-section offered within the conduit comprises a diaphragm and a cannula movably mounted within the conduit between a position away from the diaphragm corresponding to the closed position of the device and a position in which it is engaged through the diaphragm corresponding to the open condition of the device, the mechanism for adjusting the passage cross-section provided within the conduit comprises both a slide with which the cannula forms one piece, this slide being capable of being slid in relation to the body under the control of the repositioning member, and a ratchet wheel rotatably mounted with respect to the slide and fixed axially with respect to this slide, and the body comprises section members engaging the ratchet wheel in order to move it angularly when the slide slides, and section members guiding the ratchet wheel to guide it when the repositioning member is released towards at least two different axial positions corresponding to the open and closed conditions of the device, so that the cannula moves in one direction and the other alternately between its two positions under the control of the repositioning member only when the repositioning member is moved along the opening and closing paths in a control direction which is the same for the two directions in which the cannula moves, and so that both the direction of movement of the repositioning member following the closing path and the direction of movement of the repositioning member following the opening path are identical.

2. Device according to claim 1, characterised in that the direction (Z-Z) in which the repositioning member (32) moves along the said opening and closing paths is angularly offset with respect to the axis (X-X) of the conduit (14).

3. Device according to claim 1, characterised in that the conduit (14) is straight, and in that the said repositioning member (32) can be moved laterally along the said opening and closing paths parallel to the axis (X-X) of the said conduit (14).

4. Device according to claim 1, characterised in that the said repositioning mechanism (27) comprises a resilient return member (74) for the repositioning member (32) following the said opening and closing paths in the opposite direction to that bringing about repositioning of the device.

5. Device according to claim 1, characterised in that the body (12) is of a generally flattened oval shape having two opposite principal surfaces (50A, 50B) and a peripheral lateral surface connecting the said opposite principal surfaces (50A, 50B).

6. Device according to claim 5, characterised in that on its peripheral lateral surface the body has at least two adjacent hollows (52A, 52B) forming supporting surfaces for the fingers of one hand.

7. Device according to claim 6, characterised in that two hollows (52A, 52B) forming the supporting surfaces for the fingers of the hand are arranged in succession in a direction substantially parallel to the axis (X-X) of the conduit (14).

8. Device according to claim 6, characterised in that the said control member (32) projects beyond the casing (12) between two hollows (52A, 52B) forming the supporting surfaces for the fingers of the hand and the rear extremity (16) of the conduit (14).

9. Device according to claim 1, further comprising means (74, 136) for holding the device in its open condition and in its closed condition.

* * * * *